United States Patent [19]

Mandella et al.

[11] Patent Number: 5,326,880
[45] Date of Patent: Jul. 5, 1994

[54] ASYMMETRICAL POLYPYRROLIDONYL COMPOUNDS HAVING A WIDE LIQUID RANGE

[75] Inventors: William L. Mandella, Boonton; Paul D. Taylor, West Milford, both of N.J.; Terry E. Smith, Murray, Ky.

[73] Assignee: ISP Investments Inc., Wilmington, Del.

[21] Appl. No.: 26,314

[22] Filed: Mar. 2, 1993

[51] Int. Cl.$^5$ ............................................. C07D 207/12
[52] U.S. Cl. ...................................................... 548/519
[58] Field of Search ......................................... 548/519

[56] References Cited

PUBLICATIONS

CA93(20):186947m Some ... Halogenophores. Schenck et al., 1980.
CA93(10):101410j Structure ... (povidone-iodine) Schenck et al., 1980.

Primary Examiner—Mary C. Lee
Assistant Examiner—Joseph K. McKane
Attorney, Agent, or Firm—Joshua J. Ward; Marilyn J. Maue

[57] ABSTRACT

This invention relates to non-polymeric, asymmetrical, low freezing, high boiling, aliphatic compounds containing from 2 to 5 pyrrolidonyl rings and from 13 to 40 carbon atoms which melt below 0° C. and which boil above 300° C. at atmospheric pressure and to the synthesis and use of said liquid polypyrrolidonyl compounds.

11 Claims, No Drawings

ASYMMETRICAL POLYPYRROLIDONYL COMPOUNDS HAVING A WIDE LIQUID RANGE

In one aspect the invention relates to novel compounds having asymmetrical structure, melting points below 0° C. and boiling points above 300° C. which are useful as complexing and dispersing agents for agrichemicals and pharmaceutical drug formulations and as low temperature lubricants.

BACKGROUND OF THE INVENTION

Substantially symmetrical polypyrrolidonyl compounds, such as polyvinylpyrrolidone, have been used as binders and film-formers in the cosmetic arts. They have also been found to have adhesive properties in pressure sensitive applications; however, these low molecular weight vinylpyrrolidone polymers occur as solids or thick viscous gels and are not useful as solvents or dispersants for chemicals which are difficultly soluble in conventional solubilizing agents.

Other symmetrical dipyrrolidonyl compounds, such as those disclosed in the Journal of the American Oil Chemists Society, 1990, Volume 67, pages 739-742; U.S. Pat. No. 3,989,815 and U.S. Pat. No. 3,988,315 have been found to possess surfactant and complexing properties. However, these symmetrical compounds have melting points of at least 10° C. so that they are unsuitable for low temperature applications such as low temperature lubricants and dispersants or pre-emergent agricultural herbicides and the like which are preferably administered before the growing season during or after frost. Additionally, these compounds have limited use because of their tendency to foam during formulation with active chemicals.

Accordingly, it is an object of this invention to provide a dispersant or lubricant which has a melting point below 0° C. and a wide liquid range up to at least 250° C. for applications which require operation over extreme temperature conditions.

Another object of this invention is to provide a non-foaming polypyrrolidonyl liquid as an improved dispersant for agrichemicals as well as a dispersing agent for cosmetics and pharmaceutical drugs.

Another object of this invention is to provide polypyrrolidonyl compounds which retain their liquid state over a wide temperature range and which are non-toxic for agricultural, pharmaceutical and cosmetic uses.

Still another object is to provide non-polymeric liquids having boiling points above 250° C., which are compatible with a wide range of chemical additives and which do not materially alter the viscosity of a chemical composition.

Still another object is to provide a compound having the above properties which can be prepared by an economic and commercially feasible synthesis process.

These and other objects of the invention will become apparent from the following description and disclosure.

THE INVENTION

In accordance with this invention there is provided a non-foaming, non-polymeric, asymmetrical polypyrrolidonyl compound defined by the formula

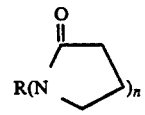

in which R is selected from the group of a $C_5$ to $C_{25}$ aliphatic hydrocarbon and a $C_5$ to $C_{25}$ aliphatic hydrocarbon ether moiety including an aliphatic polyether moiety and n is an integer having a value of from 2 to 5; which compounds have a melting point below 0° C. and a boiling point above 300° C. at atmospheric pressure. Preferred of this group are the asymmetrical liquid di-and tri- pyrrolidonyl substituted $C_5$ to $C_{12}$ alkanes and most preferred are the liquid di- and tri- pyrrolidonyl $C_5$ to $C_8$ alkanes having a boiling point above 300° C. and a melting point below −10° C. Specific examples of said high boiling polypyrrolidonyl compounds include 1,5-dipyrrolidonyl-2-methyl pentane; 1,3-dipyrrolidonyl pentane; 1,8-dipyrrolidonyl-4-pyrrolidonyl methyl octane; 1,4-dipyrrolidonyl pentane; 1,4,8-tripyrrolidonyl octane, 1,4,8-tripyrrolidonyl-3-methyl octane; 1-pyrrolidonyl-3-pyrrolidonyl methyl-3,5,5-trimethylcyclohexane; 1,6-dipyrrolidonyl-2,2,4-trimethyl hexane; 1,6-dipyrrolidonyl-2,4,4-trimethyl hexane; 1,8-dipyrrolidonyl-4-methoxymethyl triethylene glycol; 1,8-dipyrrolidonyl-4-ethyl-triethylene glycol, dipyrrolidonyl polyoxypropylene, 1-methyl-3,6-dioxa-1,8-pyrrolidonyl octane, 2-ethylpyrrolidonyltris(pyrrolidonyl) tripropylene glycol and the like which compounds have asymmetrical structure.

The compounds of this invention are economically prepared by reacting an asymmetrical aliphatic polyamine with an excess of butyrolactone (BLO) e.g. gamma-butyrolactone at a temperature of from about 225° to about 350° C., preferably 270° to 325° C., under a pressure ranging from atmospheric up to 1000 psi, preferably from about 300 to about 600 psi within a period of from 1 to 12 hours, more often from 3 to 9 hours. The amount of BLO employed in the condensation reaction is dependent on the number of amino groups in the polyamine coreactant. Generally, the butyrolactone is used in about a 1.05 to about 2.5 moles/mole of each amino group preferably a 1.1 to 1.8 moles with respect to each amino group. The synthesis reaction using BLO can be described by the general equation

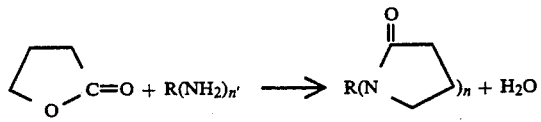

wherein n' is equal to n.

Examples of suitable asymmetrical polyamines include $C_5$ to $C_{25}$ alkanes substituted with 2 to 5 amino groups and $C_5$ to $C_{25}$ alkyl ethers and polyethers substituted with 2 to 5 amino groups such as 1,5-diamino-2-methyl pentane; 1,3-diaminopentane; 1,4,8-triamino octane; 1,4,8,12-tetraamino dodecane; 1,3,8,10-tetraamino-6-ethylamino-dodecane; 3-aminomethyl-3,5,5-trimethyl cyclohexylamine; 1,6-diamino-2,2,4-trimethyl hexane; 1,6-diamino-2,4,4-trimethyl hexane; 4-methoxy-1,8-diamino triethylene glycol; 4-ethyl-1,8-diamino triethylene glycol; 1,4,12-triamino tetraethylene glycol; 1,3,8-triaminodecyl-8-amino octyl ether; 1,3-diaminopentyl-1,4,8-triamino octyl ether; isopropylamino oxypropylene amine; ethylamino poly(oxypropylene)amine; 2-ethylamino-tris(amino) tripropylene glycol compounds and the like.

The above reaction can be carried out in the presence or absence of a solvent. When employed, suitable solvents include benzene, toluene, xylene, a substantially higher excess of butyrolactone and other liquid solvents which are inert in the reaction. The synthesis is easily effected in the absence of any catalyst and provides direct conversion of the asymmetrical aliphatic polyamine to the corresponding polypyrrolidonyl product which is easily separated and recovered by distillation.

The products of the present invention possess boiling points above 250° C. at atmospheric pressure and melting points below 0° C., thus, they are ideally suitable as dispersing or emulsifying agents for products such as high or low temperature adhesives, paint finishes and lubricant compositions used in aerospace or arctic research which are subject to wide temperature variations. The present products are also useful as automotive lubricants and as high temperature polymerization media. The present compounds are useful individually or in admixture and may be added to existing formulations in an amount up to about 10 wt. % to improve or impart dispersing or lubricating properties. Also, they may be employed in greater amounts when used as a lubricant. Many other uses and applications will become apparent to those skilled in the art.

Having generally described the invention, reference is now had to the following examples which illustrate preferred embodiments but which are not to be construed as limiting to the scope of the invention as more broadly defined above and in the appended claims.

EXAMPLE 1

Into a 1-liter stainless steel autoclave was introduced 206.6 g of gamma-butyrolactone (BLO) and 116.2 g of 2-methyl-1,5-diaminopentane to provide a mole ratio of about 2.4:1. The autoclave was sealed and purged with $N_2$ after which the contents were heated to 275° C. and held at that temperature for 8 hours during which time the reaction mixture was agitated and the pressure increased from atmospheric to about 480 psig. The reaction produced a liquid product which was recovered from the autoclave and distilled to recover 1,5-dipyrrolidonyl-2-methyl pentane,

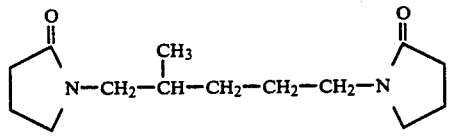

as a yellow liquid at a boiling point of 180°–185° C. at 0.30–0.45 mm Hg.

EXAMPLE 2

The procedure described in Example 1 was repeated except that 102.0 g 1,3-diaminopentane and 206.4 g of BLO were used (the mole ratio of BLO to asymmetrical diamine was about 2.4:1). The reaction product was distilled to recover 1,3-bis(pyrrolidonyl)pentane,

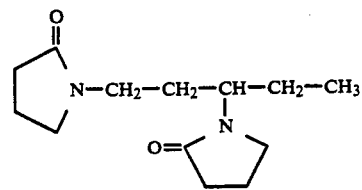

as a yellow liquid at a boiling point of 190°–195° C. at 0.80–0.95 mm Hg.

EXAMPLE 3

The procedure described in Example 1 was repeated except that 173.3 g 4-aminomethyl-1,8-diamino octane and 310.0 g of BLO were employed (the mole ratio of BLO to asymmetrical triamine was about 3.6:1) and the reaction was heated 8 hours at 300° C. The reaction product was distilled to recover 4-(pyrrolidonylmethyl)-1,8-bis(pyrrolidonyl)octane,

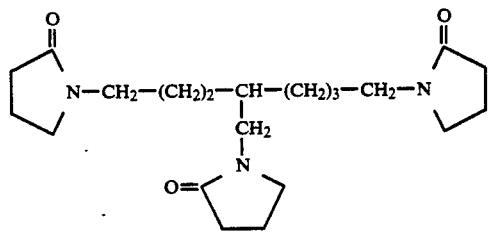

as a yellow liquid having a boiling point of 288°14 290° C. at 0.5–0.7 mm Hg.

EXAMPLE 4

The procedure described in Example 1 is repeated except that 136.0 g. of 1-methyl-3,6-dioxa-1,8-diamino octane and 173.9 g of BLO are used (the mole ratio of BLO to asymmetrical diamine is about 2.5:1). The reaction product is distilled to recover 1-methy-3,6-dioxa-1,8-dipyrrolidonyl octane,

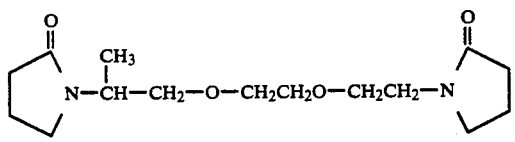

as a yellow liquid having a boiling point of about 210°–220° C. at 0.20–0.45 mm Hg. When example 4 is repeated with ethylamino-amino poly(2-3)oxypropylene amine (MW~230) the corresponding product, N-ethylpyrrolidonyl-pyrrolidonyl polyoxypropylene

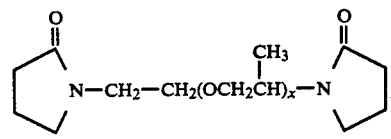

mixture X=2-3 is produced and when example 4 is repeated with 2-ethylamino-tris(amino) tripropylene glycol the corresponding 2-ethylpyrrolidonyl tris(pyrrolidonyl)tripropylene glycol

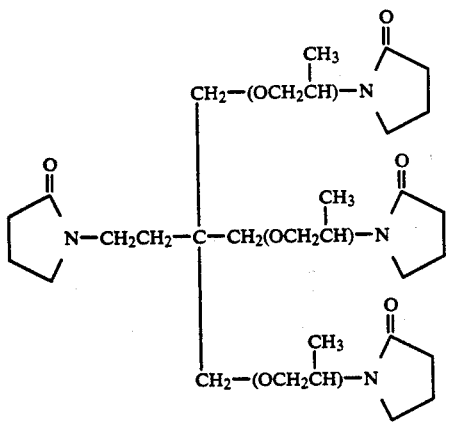

is produced.

What is claimed is:

1. A non-polymeric, asymmetrical compound having a freezing point below 0° C. and a boiling point above 300° C. at atmospheric pressure and having the formula

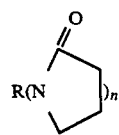

wherein R in the asymmetrical structure is selected from the group of a $C_5$ to $C_{25}$ aliphatic hydrocarbon, and a $C_5$ to $C_{25}$ aliphatic hydrocarbon ether or polyether and n is an integer having a value of from 2 to 5.

2. A non-polymeric, asymmetrical compound having a freezing point below 0° C. and a boiling point above 300° C. at atmospheric pressure and having the formula

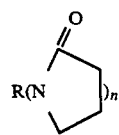

wherein R is the asymmetrical structure is selected from the group of a $C_5$ to $C_{25}$ aliphatic hydrocarbon, and a $C_5$ to $C_{25}$ aliphatic hydrocarbon ether of polyether and n is an integer having a value of 3.

3. A non-polymeric, asymmetrical compound having a freezing point below 0° C. and a boiling point above 300° C. at atmospheric pressure and having the formula

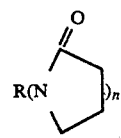

wherein R in the asymmetrical structure is selected from the group of a $C_5$ to $C_{25}$ aliphatic hydrocarbon ether or polyether and n is an integer having a value of from 2 to 5.

4. The asymmetrical compound of claim 2 wherein R is alkyl and said alkyl contains from 5 to 12 carbon atoms.

5. The asymmetrical compound of claim 2 wherein said alkyl contains from 5 to 8 carbon atoms.

6. The compound of claim 4 having the formula

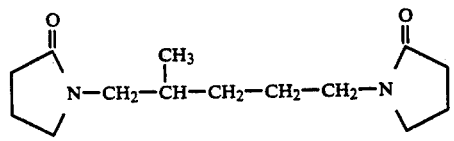

7. The compound of claim 4 having the formula

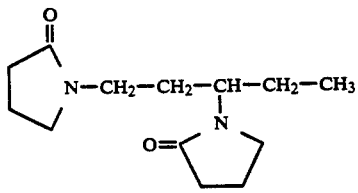

8. The compound of claim 2 having the formula

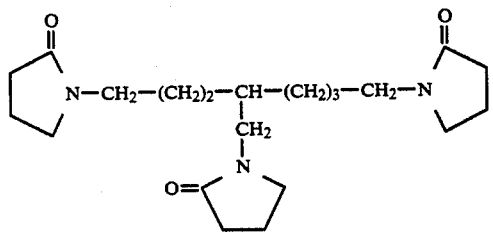

9. The compound of claim 3 having the formula

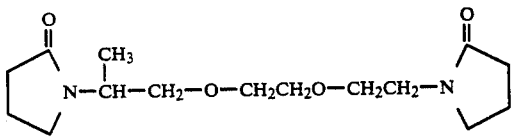

10. A mixture of compounds of claim 3 having the formula

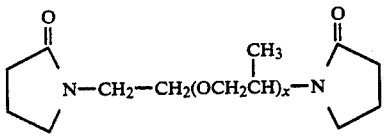

wherein X has an average value of 2–3.

11. The compound of claim 3 having the formula

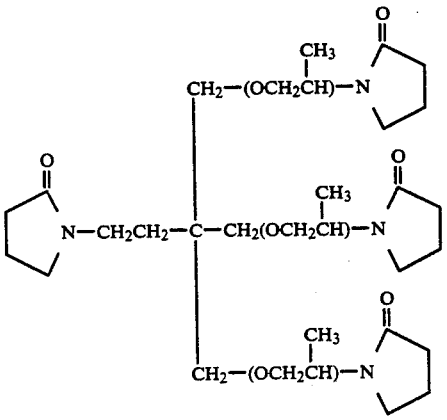

* * * * *